(12) United States Patent
Maltz

(10) Patent No.: US 11,433,258 B2
(45) Date of Patent: Sep. 6, 2022

(54) SYSTEM AND METHOD FOR DOSE MEASUREMENT IN RADIATION THERAPY

(71) Applicant: UIH-RT US LLC, Walnut Creek, CA (US)

(72) Inventor: Jonathan Maltz, Walnut Creek, CA (US)

(73) Assignee: UIH-RT US LLC, Walnut Creek, CA (US)

( * ) Notice: Subject to any disclaimer, the term of this patent is extended or adjusted under 35 U.S.C. 154(b) by 250 days.

(21) Appl. No.: 16/658,004

(22) Filed: Oct. 18, 2019

(65) Prior Publication Data

US 2021/0113857 A1    Apr. 22, 2021

(51) Int. Cl.
*A61N 5/10*    (2006.01)
*A61B 6/00*    (2006.01)

(52) U.S. Cl.
CPC .......... *A61N 5/1071* (2013.01); *A61B 6/5282* (2013.01); *A61N 5/103* (2013.01); *A61N 5/1045* (2013.01)

(58) Field of Classification Search
CPC ...... A61N 5/10–1084; A61N 2005/1085–1098
See application file for complete search history.

(56) References Cited

U.S. PATENT DOCUMENTS

| | | |
|---|---|---|
| 2007/0041499 A1 | 2/2007 | Lu et al. |
| 2008/0031406 A1 | 2/2008 | Yan et al. |
| 2012/0230462 A1 | 9/2012 | Robar et al. |
| 2013/0188856 A1 | 7/2013 | Adler, Jr. et al. |
| 2016/0125602 A1 | 5/2016 | Winfield et al. |
| 2016/0213951 A1 | 7/2016 | Uhlemann et al. |
| 2016/0256712 A1 | 9/2016 | Vahala et al. |

(Continued)

FOREIGN PATENT DOCUMENTS

CN    104548372 A    4/2015

OTHER PUBLICATIONS

J. S. Maltz et al., "Algorithm for X-ray Scatter, Beam-Hardening and Beam Profile Correction in Dagnostic (Kilovoltage) and Treatment (Megavoltage) Cone Beam CT.," IEEE Transactions on Medical imaging, 27(12): 1791-1810, 2008.

(Continued)

*Primary Examiner* — Thaddeus B Cox
(74) *Attorney, Agent, or Firm* — Metis IP LLC

(57) ABSTRACT

The present disclosure provides a system and method for dose measurement in radiation therapy. The method may include obtaining a beam model and a detector model related to a radiation device, and a reference image and a treatment plan related to the subject, and determining a synthetic image based on the beam model, the detector model, and the reference image. The method may also include obtaining a treatment image by performing at least a portion of the treatment plan including delivering at least a radiation beam toward the subject using the radiation device, and determining one or more scaling factors. The method may further include determining a synthetic estimate of the treatment image based on the synthetic image and the one or more scaling factors. The method may further include estimating radiation dose deposition based on the treatment image and the synthetic estimate of the treatment image.

20 Claims, 7 Drawing Sheets

(56) References Cited

U.S. PATENT DOCUMENTS

| | | |
|---|---|---|
| 2017/0189719 A1 | 7/2017 | Liu et al. |
| 2017/0189720 A1 | 7/2017 | Liu et al. |
| 2017/0189724 A1 | 7/2017 | Liu et al. |
| 2018/0243586 A1* | 8/2018 | Ramezanzadeh Moghadam ........ G16H 20/40 |
| 2020/0206539 A1* | 7/2020 | Han .................... A61N 5/1071 |
| 2020/0353287 A1 | 11/2020 | Maltz |

OTHER PUBLICATIONS

First Office Action in Chinese Application No. 202010557608.X dated Jan. 24, 2022, 12 pages.

* cited by examiner

SYSTEM AND METHOD FOR DOSE MEASUREMENT IN RADIATION THERAPY

TECHNICAL FIELD

The present disclosure generally relates to systems and methods for radiation therapy, and more particularly, to systems and methods of radiation dosimetry in a radiation therapy.

BACKGROUND

Radiation therapy is widely used in cancer therapy and several other health conditions. Usually, a radiation therapy treatment plan (also referred to herein as a treatment plan) for a cancer patient is generated before treatment starts. Treatment may be delivered, according to the treatment plan, to the patient in several treatment fractions, spreading over a treatment period of multiple days. For one or more factors including, e.g., actual patient setup (e.g., positioning) during a treatment fraction different from a planned patient setup, an actual dose delivered to the patient may be different from the planned dose. Accordingly, the errors may need to be detected and the actual dose delivered to the patient may need to be calculated. Thus, it may be desirable to develop systems and methods for measuring an actual dose delivered during treatment.

SUMMARY

In a first aspect of the present disclosure, a system is provided. The system may include at least one storage medium including a set of instructions, and at least one processor in communication with the at least one storage medium. When executing the set of instructions, the at least one processor may be configured to direct the system to perform operations including obtaining a beam model and a detector model related to a radiation device, a reference image related to a subject, and a treatment plan related to the subject; determining a synthetic image based on the beam model, the detector model, and the reference image; obtaining a treatment image by performing at least a portion of the treatment plan including delivering at least a radiation beam toward the subject using the radiation device; determining one or more scaling factors; determining a synthetic estimate of the treatment image based on the synthetic image and the one or more scaling factors; and estimating radiation dose deposition based on the treatment image and the synthetic estimate of the treatment image.

In a second aspect of the present disclosure, a system is provided. The system may include at least one storage medium including a set of instructions, and at least one processor in communication with the at least one storage medium. When executing the set of instructions, the at least one processor may be configured to direct the system to obtaining a beam model related to a radiation device, a reference image related to a subject, and a treatment plan related to the subject; determining a first synthetic image and a first treatment image under a first condition; determining a second synthetic image and a second treatment image under a second condition, wherein the second condition is that at least a portion of the treatment plan is performed on the subject; determining a first ratio based on the first synthetic image and the second synthetic image; determining a second ratio based on the first treatment image and the second treatment image; determining a difference or ratio by comparing the first ratio and the second ratio; and detecting an error in a radiation therapy based on the difference or the ratio.

In a third aspect of the present disclosure, a method is provided. The method may be implemented on a computing apparatus having at least one processor and at least one computer-readable storage device. The method may include obtaining a beam model and a detector model related to a radiation device, a reference image related to a subject, and a treatment plan related to the subject; determining a synthetic image based on the beam model, the detector model, and the reference image; obtaining a treatment image by performing at least a portion of the treatment plan including delivering at least a radiation beam toward the subject using the radiation device; determining one or more scaling factors; determining a synthetic estimate of the treatment image based on the synthetic image and the one or more scaling factors; and estimating radiation dose deposition based on the treatment image and the synthetic estimate of the treatment image.

In a fourth aspect of the present disclosure, a method is provided. The method may be implemented on a computing apparatus having at least one processor and at least one computer-readable storage device. The method may include obtaining a beam model related to a radiation device, a reference image related to a subject, and a treatment plan related to the subject; determining a first synthetic image and a first treatment image under a first condition; determining a second synthetic image and a second treatment image under a second condition, wherein the second condition is that at least a portion of the treatment plan is performed on the subject; determining a first ratio based on the first synthetic image and the second synthetic image; determining a second ratio based on the first treatment image and the second treatment image; determining a difference or ratio by comparing the first ratio and the second ratio; and detecting an error in a radiation therapy based on the difference or the ratio.

In a fifth aspect of the present disclosure, a non-transitory computer readable medium may store instructions, the instructions, when executed by at least one processor, the at least one processor may be configured to perform operations including obtaining a beam model and a detector model related to a radiation device, a reference image related to a subject, and a treatment plan related to the subject; determining a synthetic image based on the beam model, the detector model, and the reference image; obtaining a treatment image by performing at least a portion of the treatment plan including delivering at least a radiation beam toward the subject using the radiation device; determining one or more scaling factors; determining a synthetic estimate of the treatment image based on the synthetic image and the one or more scaling factors; and estimating radiation dose deposition based on the treatment image and the synthetic estimate of the treatment image.

In a sixth aspect of the present disclosure, a non-transitory computer readable medium may store instructions, the instructions, when executed by at least one processor, the at least one processor may be configured to perform operations including obtaining a beam model related to a radiation device, a reference image related to a subject, and a treatment plan related to the subject; determining a first synthetic image and a first treatment image under a first condition; determining a second synthetic image and a second treatment image under a second condition, wherein the second condition is that at least a portion of the treatment plan is performed on the subject; determining a first ratio based on the first synthetic image and the second synthetic image; determining a second ratio based on the first treatment image and the second treatment image; determining a difference or ratio by comparing the first ratio and the second ratio; and detecting an error in a radiation therapy based on the difference or the ratio.

In some embodiments, to estimate radiation dose deposition based on the treatment image and the synthetic estimate of the treatment image, the system may further directed to perform the operations including determining a difference or ratio between the treatment image and the synthetic estimate of the treatment image.

In some embodiments, the system is further directed to perform the operations including determining a primary component in the treatment image by performing a scatter correction of the treatment image, wherein the estimating radiation dose deposition is performed based on the primary component in the treatment image.

In some embodiments, to estimate the radiation dose deposition based on the primary component in the treatment image and the synthetic estimate of the treatment image, the system is further configured to perform the operations including converting the primary component into an energy distribution in an exit phase space; and estimating the radiation dose deposition based on the energy distribution in the exit phase space.

In some embodiments, to estimate the radiation dose deposition based on the energy distribution in the exit phase space, the system is further configured to perform the operations including, in a plurality of iterations, determining an optimal gantry position corresponding to a smallest discrepancy among discrepancies between the primary component in the treatment image and the synthetic image in the plurality of iterations, wherein the optimal gantry position is associated with a sequence of MLC shapes, jaw positions, and collimator angles.

In some embodiments, the beam model relates to at least one of an energy of the particles of the radiation beam, charges of the particles, types of the particles, or travel directions of the particles.

In some embodiments, the detector model relates to at least one of a response of a detector of the radiation device to particles of a type, a response of the detector to particles of an energy level, an optical response of the detector, or a temporal response of the detector.

In some embodiments, the detector model relates to a material of a detector of the radiation device and a density distribution of the material of the detector.

In some embodiments, the one or more scaling factors relate to different shapes of one or more fields or segments of the treatment plan.

In some embodiments, the first condition is that at least part of the treatment plan is performed without the subject being present.

In some embodiments, the first condition is that at least part of the treatment plan is performed on an object.

In some embodiments, the first synthetic image is determined by simulating a first imaging condition of the first treatment image, and the second synthetic image is determined by simulating a second imaging condition of the second treatment image.

In some embodiments, the error includes at least one of an error in the field shape and an intensity modulation pattern, an error in patient setup, or an error in beam quality.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
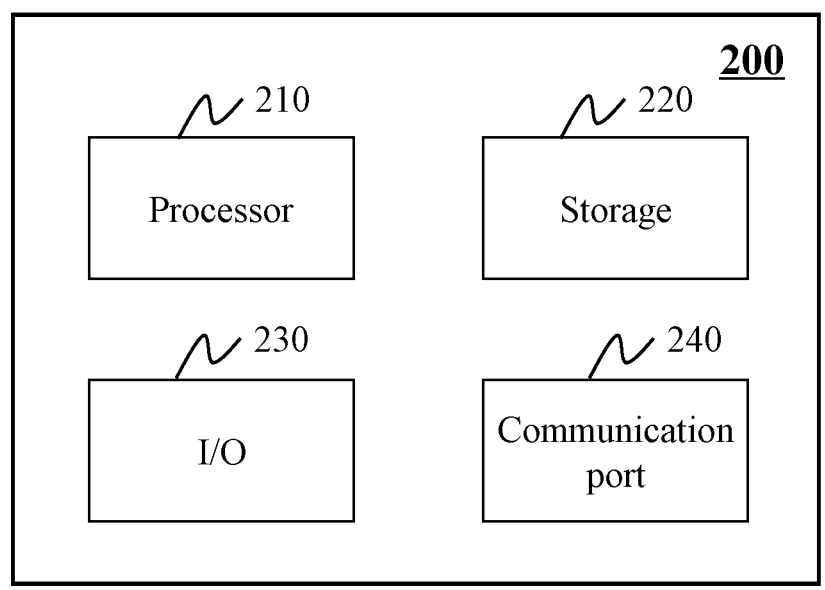
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging and/or treatment, such as for disease diagnosis, treatment or research purposes. In some embodiments, the system may be a radiation therapy system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy. The term "image" used in this disclosure may refer to a 2D image, a 3D image, or a 4D image. In some embodiments, the term "image" may refer to an image of a region, e.g., a region of interest (ROI), of a patient. The term "region of interest" or "ROI" used in this disclosure may refer to a part of an image along a line, in two spatial dimensions, in three spatial dimensions, or any of the proceeding as they evolve as a function of time. The image may be an EPID (Electronic Portal Image Device) image, a CT image, a fluoroscopy image, an ultrasound image, a PET image, or an MRI image. This is not intended to limit the scope of the present disclosure. For persons having ordinary skills in the art, a certain number of variations, changes, and/or modifications may be deduced under the guidance of the present disclosure. Those variations, changes, and/or modifications do not depart from the scope of the present disclosure.

Before a patient receives radiation therapy, a planning image may be taken, and a treatment plan may be designed for the patient based on the planning image. A guide image may be taken to guide radiation delivery during or before the radiation therapy (e.g., on the day of treatment, or hours before the treatment, or minutes before the treatment, or seconds before the treatment, or during the treatment). However, an actual dose delivered to the patient during a treatment fraction may be different from the planned dose corresponding to the treatment period due to one or more factors including, e.g., an actual patient setup (e.g., positioning) during a treatment fraction different from a planned subject setup, motion of one or more components of the image-guided treatment apparatus 110 (e.g., one or more components of a treatment component of the image-guided treatment apparatus 110) different from what is needed to implement the treatment fraction of the treatment plan, unanticipated or anticipated motion of internal organs, radiation that is scattered or otherwise fails to reach the target portion (e.g., a tumor) of the subject. In this connection, embodiments of the present disclosure relate to systems and methods for measuring an actual dose delivered during treatment.

According to some embodiments of the present disclosure, before the treatment plan is prescribed, a planning image of the treatment plan regarding a subject may be obtained. A beam model and a detector model related to a radiation device may be obtained. A synthetic image based on the beam model, the detector model, and the planning image be determined. A treatment image may be obtained by performing at least a portion of the treatment plan on the subject. One or more scaling factors may be determined. A synthetic estimate of the treatment image may be determined based on the synthetic image and the one or more scaling factors. Then an actual radiation dose deposition by the delivery of a treatment fraction may be estimated based on the treatment image and the synthetic estimate of the treatment image.

Figure 1:
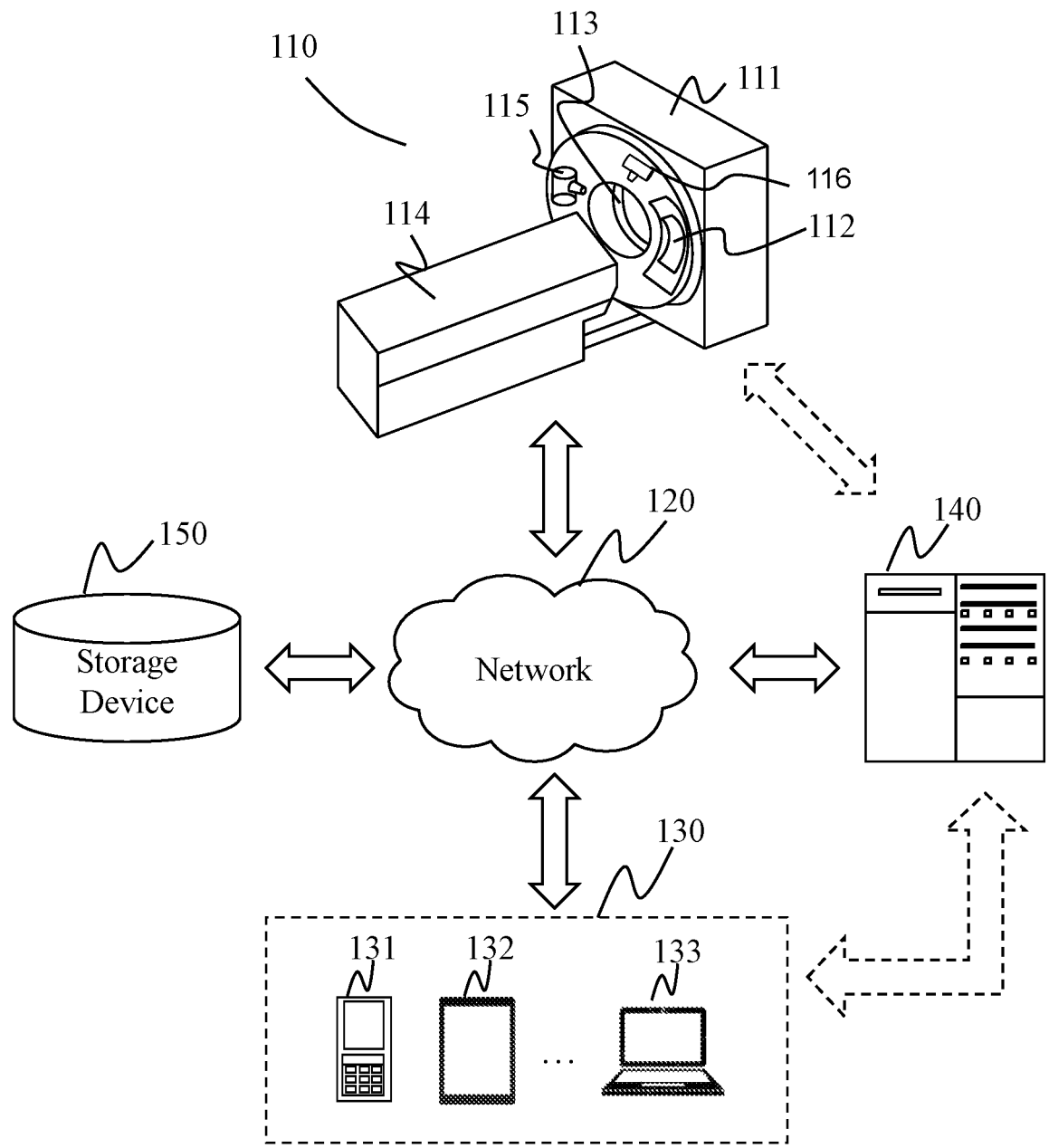
FIG. 1 is a schematic diagram illustrating an exemplary radiation therapy system according to some embodiments of the present disclosure.

FIG. 1 is a schematic diagram illustrating an exemplary radiation therapy system 100 according to some embodiments of the present disclosure. The radiation therapy system 100 may include an image-guided treatment apparatus 110, a network 120, one or more terminals 130, a processing device 140, and a storage device 150.

The image-guided treatment apparatus 110 may include an imaging component, a treatment component, a gantry 111, a table (also referred to as treatment couch) 114, an imaging region 113, or the like. The imaging component may include an imaging-radiation source 115, a detector 112, or the like. The treatment component may include a treatment radiation source 116, an accelerator (not shown in FIG. 1), or the like. The gantry 111 may be configured to accommodate the imaging component and the treatment component. A subject may be placed on the table 114 for radiation treatment and/or imaging scan.

The imaging component may generate an image of the subject before, during and/or after a treatment fraction. The imaging component may include a computed tomography (CT) component, an ultrasound imaging component, a fluoroscopy imaging component, a magnetic resonance imaging (MRI) component, a single photon emission computed tomography (SPECT) component, a positron emission tomography (PET) component, or the like, or any combination thereof.

The imaging-radiation source 115 may emit radiation to the subject. The detector 112 may detect radiation events (e.g., x-ray photons, gamma-ray photons) emitted from the imaged region 113. In some embodiments, the detector 112 may include one or more detector units. The detector units may include a scintillation detector (e.g., a cesium iodide detector, a gadolinium oxysulfide detector), a gas detector, etc. The detector unit may include a single-row detector and/or a multi-rows detector.

In some embodiments, the imaging component may be a cone beam CT (CBCT) imaging component. The CBCT imaging component may perform a CBCT scan on the subject by emitting cone beam X-rays to the subject. In some embodiments, the imaging component may be a multi-slice CT (MSCT) imaging component. The MSCT imaging component may perform an MSCT scan on the subject. In some embodiments, the imaging component may be an integrated CT imaging component that can perform a CBCT scan and an MSCT scan on the subject. An MSCT scan is comprised of one or more axial slices of the imaged object (usually a patient, a human, an animal subject).

The treatment component may deliver radiation treatment to the subject. The treatment radiation source 116 may emit treatment radiations towards the subject. The therapy radiations may be in forms of particles, which may be accelerated by, for example, an accelerator (not shown in FIG. 1) and irradiate on the subject.

In some embodiments, the image-guided treatment apparatus 110 may include two gantries that house the imaging component and the treatment component, respectively. The imaging component (e.g., the imaging-radiation source 115 and the detector 112) and the corresponding gantry may be spaced at a distance from the treatment component (e.g., the treatment radiation source 116) and the corresponding gantry. In some embodiments, the corresponding gantry of the imaging component and the corresponding gantry of the imaging component may have collinear bore. For example, a bore of the imaging component gantry and a bore of the treatment component gantry may share a same axis of rotation. The subject may be positioned in different positions in the table 114 for imaging and treatment. In some embodiments, the imaging-radiation source 115 and the treatment radiation source 116 may be integrated as one radiation source for imaging and/or treatment.

In some embodiments, the radiation therapy system 100 may include a radiation treatment device, and a CT scanner. Descriptions of such devices may be found in, e.g., US Application Publication Nos. 20170189720A1 and 20170189724A1 both entitled "Radiation Therapy System," and US Application Publication No. 20170189719A1 entitled "Radiation Therapy Positioning System," the contents of each of which are hereby incorporated by reference. The radiation treatment device may include one or more components that is the same as or substantially similar to those of the image-guided treatment apparatus 110. For example, the radiation treatment device may include the same components as the image-guided treatment apparatus 110. As another example, the radiation treatment device may include a treatment component, a gantry, a table, and a detecting region. In some embodiments, the radiation treatment device may be a general treatment device.

In some embodiments, the CT scanner may be a CBCT scanner and/or an MSCT scanner. The CBCT scanner may perform a CBCT scan of a subject. The MSCT scanner may perform an MSCT scan of a subject. The images generated based on the CBCT scan or the MSCT scan may be stored in a storage device in the radiation therapy system 100 for adaptive radiation therapy planning. The CBCT scanner or the MSCT scanner may include one or more components of a CT scanner known to a person of ordinary skill in the art.

For example, the CBCT scanner may include a gantry, a detector, a detecting region, a table, and a CBCT radiation-emitting scanning source.

Merely by way of example, the radiation therapy system 100 may include an MSCT scanner and a radiation treatment device including a CBCT imaging component and a treatment component. The MSCT scanner may perform an MSCT scan of a subject. The radiation treatment device including the CBCT imaging component and the treatment component may perform a CBCT scan and/or treat the subject. Additionally or alternatively, the radiation therapy system 100 may include a CBCT scanner and a radiation treatment device including an MSCT imaging component and a treatment component. The bore of the MSCT imaging component may share an axis of rotation with the treatment component.

The network 120 may include any suitable network that can facilitate the exchange of information and/or data for the radiation therapy system 100. In some embodiments, one or more components of the radiation therapy system 100 (e.g., the image-guided treatment apparatus 110, the terminal 130, the processing device 140, the storage device 150, etc.) may communicate information and/or data with one or more other components of the radiation therapy system 100 via the network 120. For example, the processing device 140 may obtain image data from the image-guided treatment apparatus 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation therapy system 100 may be connected to the network 120 to exchange data and/or information.

Figure 3:
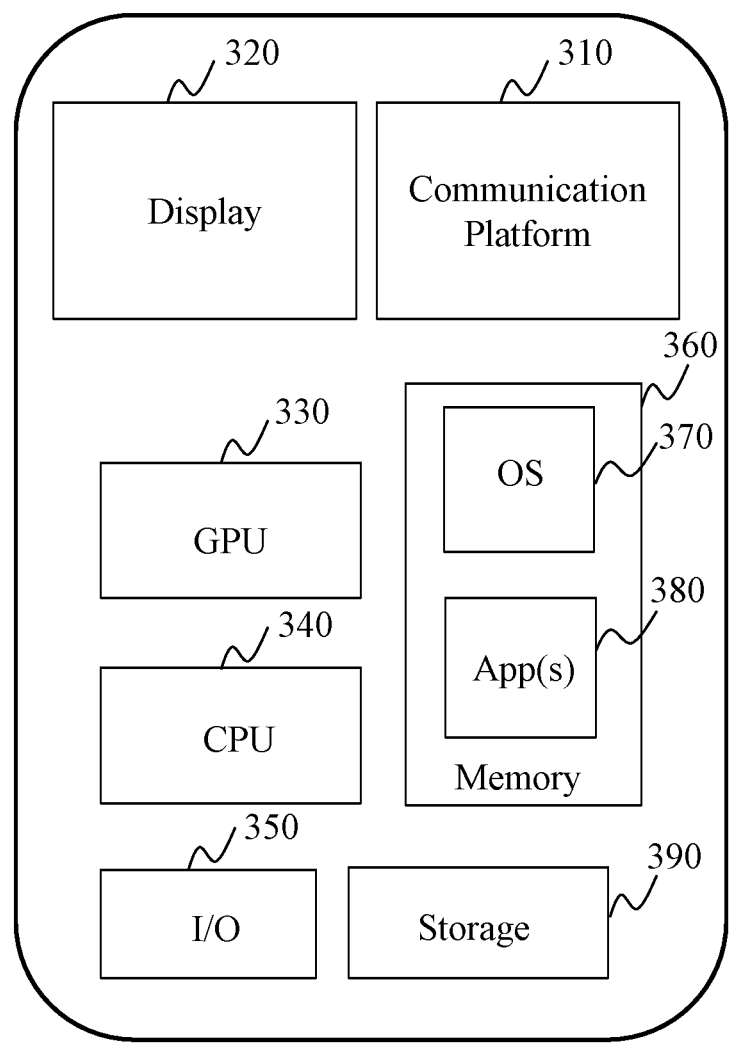
FIG. 3 is a schematic diagram illustrating hardware and/or software components of an exemplary mobile device according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the image-guided treatment apparatus 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the image-guided treatment apparatus 110, the terminal 130, and/or the storage device 150 via the network 120. As another example, the processing device 140 may be directly connected to the image-guided treatment apparatus 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the radiation therapy system 100 (e.g., the processing device 140, the terminal 130). One or more components of the radiation therapy system 100 may access the data or instructions stored in the storage device 150 via the network 120. In some embodiments, the storage device 150 may be directly connected to or communicate with one or more other components of the radiation therapy system 100 (e.g., the processing device 140, the terminal 130). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the image-guided treatment apparatus 110, the terminal 130, the storage device 150, and/or any other component of the radiation therapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is illustrated in the computing device 200 in FIG. 2. However, it should be noted that the computing device 200 in the present disclosure may also include multiple processors, and thus operations and/or method steps that are performed by one processor as described in the present disclosure may also be jointly or separately performed by the multiple processors. For example, if in the present disclosure the processor of the computing device 200 executes both operations A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the image-guided treatment apparatus 110, the terminal 130, the storage device 150, and/or any other component of the radiation therapy system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the image-guided treatment apparatus 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation therapy system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
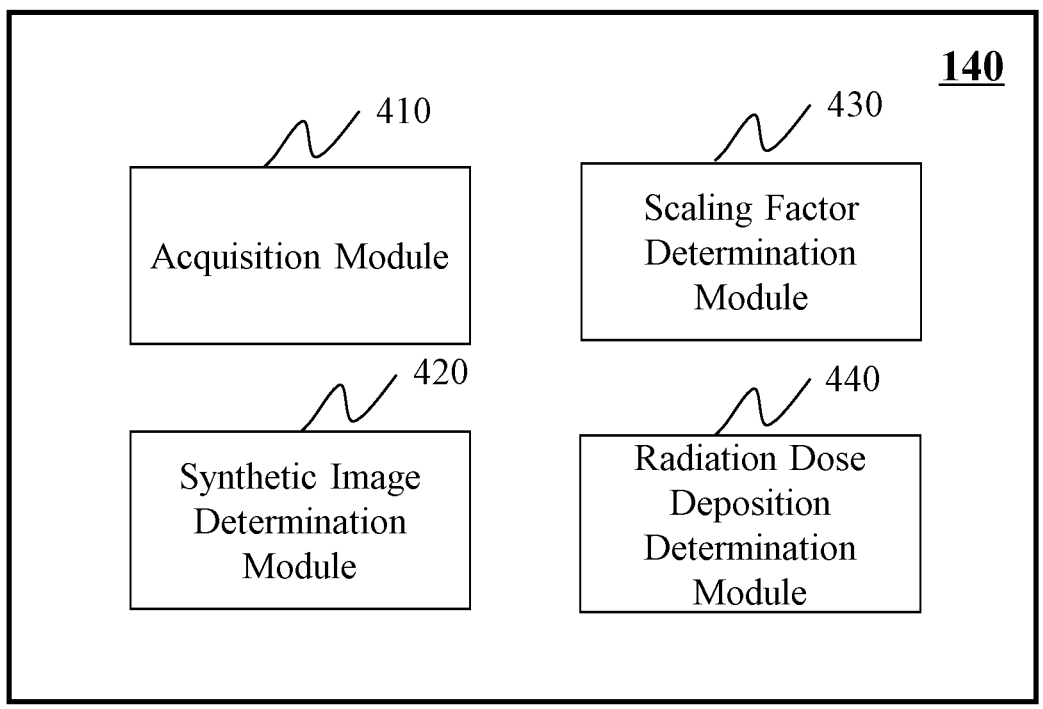
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may include an acquisition module 410, a synthetic image determination module 420, a scaling factor determination module 430, and a radiation dose deposition estimating module 440. The processing device 140 may be implemented on various components (e.g., the processor 210 of the computing device 200 as illustrated in FIG. 2).

The acquisition module 410 may acquire data. The acquisition module 410 may acquire data from the image-guided treatment apparatus 110, the storage device 150, the terminal 130, or any devices or components capable of storing data via the network 120. For example, the acquisition module 410 may acquire data from a medical cloud data center (not shown) via the network 120. The acquired data may include scanning data (e.g., CT data), planning data (e.g., a treatment plan), processed results (e.g., a reference image), user instructions, algorithms, models (e.g., a beam model and/or a detector model related to a radiation device (e.g., the image-guided treatment apparatus 110)), program codes, or the like, or a combination thereof. In some embodiments, the acquisition module 410 may acquire scanning data from the the image-guided treatment apparatus 110, more particularly, from the imaging component of the image-guided treatment apparatus 110. The scanning data may be generated by scanning the subject using an imaging scanner. The planning data may include a treatment plan. The treatment plan may include a set of parameters describing how radiation is to be delivered to a subject, including, e.g., the beam dimension or the aperture size of a beam shaping device (e.g., a collimator system of the treatment component of the image-guided treatment apparatus 110), a radiation dose distribution (i.e., spatial distribution of the radiation dose), a radiation duration, a position of a radiation target in the subject of the treatment plan or a fraction thereof, or the like, or a combination thereof. One or more reference images (e.g., treatment images) may be generated when the treatment component of the image-guided treatment apparatus 110 delivers radiation to the subject according to treatment plan. In some embodiments, the treatment image may be an EPID image. The EPID image may be generated based on energy deposited in the EPID. The beam model related to the radiation device may be a mathematical characterization in terms of a plurality of parameters that describe the radiation therapy device (e.g., the image-guided treatment apparatus 110). The plurality of parameters may include or relate to, for example, the characteristics of the accelerator (e.g., energy spectrum, lateral beam quality variations) of the treatment component of the image-guided treatment apparatus 110, the shape(s) and position(s) of one or more radiation sources, and the geometry and material of a beam shaping device (e.g., a collimator system of the treatment component of the image-guided treatment apparatus 110). The detector model related to the radiation device may be used to generate a synthetic image based on the interation of particles with the detector. In some embodiments, the detector model may relate to at least one of a response of a detector to particles of a type, a response of the detector to particles of an energy level, an optical response of the detector, or a temporal response of the detector.

The acquisition module 410 may transmit the acquired data to a storage device (e.g., the storage module 430, the storage device 130, etc.) for storage. The data may be stored in the form of voxel information, images, vectors, or the like, or any combination thereof. In some embodiments, the acquisition module 410 may transmit the acquired data to a computing device (including, for example, the synthetic image determination module 420, the scaling factor determination module 430, and/or the radiation dose deposition estimating module 440) for processing.

The synthetic image determination module 420 may determine a synthetic image of a subject. In some embodiments, the synthetic image determination module 420 may obtain data from the acquisition module 410, and determine the synthetic image of the subject based on the obtained data. For example, the synthetic image determination module 420 may determine the synthetic image based on the beam model, the detector model, and the reference image. The synthetic image may describe radiation energy deposited in the plane of a detector (e.g., the detector 112). In some embodiments, the synthetic image may be generated by any technique that models radiation transport through the detector (e.g., MC simulation, Boltzmann transport equations).

The scaling factor determination module 430 may determine one or more scaling factors. The one or more scaling factors may represent a relationship between a measured image (also referred to as a treatment image) and a synthetic image. In some embodiments, the scaling factor determination module 430 may determine the one or more scaling factors under a condition that the measured image and the synthetic image are generated under a same imaging condition (e.g., a calibration condition). The scaling factor between a measured image and a synthetic image may be equal to the ratio of the value of a pixel in the measured image based on a signal detected by the real detector (or an average value of multiple pixels in the measured image) and the value of a corresponding pixel in the synthetic image estimated based on a simulated detector (or an average value of multiple pixels in the synthetic image).

A scaling factor may be a constant in the case of the perfect model. The scaling factor may be field-shape-independent (i.e., uncorrelated to the shape of the radiation field or segment), and constant across the detector. In some embodiments, the synthetic image may lack sufficient details to account for an output factor relating to, e.g., the size of the radiation field (also referred to as field size) and/or the shape of the radiation field or segment (also referred to as field shape), or the like, or a combination thereof. Extra radiation that is backscattered by the collimator system such that the extra radiation enters the treatment component of the radiation therapy system 100 but fails to reach the subject or a portion thereof (e.g., the target of the subject), resulting in a variation of the value of the scaling factor between different fields. In this case, the scaling factor may be dependent on the field shape.

The radiation dose deposition estimating module 440 may estimate radiation dose deposition in the subject. In some embodiments, the radiation dose deposition estimating module 440 may obtain the synthetic image and the one or more scaling factors from the synthetic image determination module 420 and the scaling factor determination module 430, respectively, and determine a synthetic estimate of the treatment image based on the synthetic image and the one or more scaling factors.

The radiation dose deposition estimating module 440 may estimate the radiation dose deposition based on the treatment image and the synthetic estimate of the treatment image. In some embodiments, radiation deposited in the patient may include primary radiation and scattered radiation. The primary radiation may also be referred to a primary component of the radiation. The scattered radiation may also be referred to as a scatter component of the radiation. In some embodiments, the primary component in the treatment image of a subject (e.g., the patient) may be determined by subtracting the scatter component from the measured image of the subject. In some embodiments, the scatter component may be estimated by an MC simulation based on the treatment plan, the beam model, the detector model, and the reference image of the subject. In the MC simulation, images due to primary radiation and scattered radiation may be synthesized separately. In some embodiments, the scatter component may be estimated iteratively using techniques such as scatter kernel superposition (SKS), which do not need to involve the estimation of the scatter component based on a CT image.

In some embodiments, the radiation dose deposition estimating module 440 may estimate the radiation dose deposited within the patient by adjusting at least one of the field shape, the field MU, and the field MU rate based on the recorded field shape. In some embodiments, the field MU may be adjusted between a measured field MU and an expected field MU. In some embodiments, the field MU rate may also be adjusted between a measured field MU rate and an expected field MU rate. The adjusted field shape, field MU and/or field MU rate may be input into a forward radiation transport model to calculate the dose deposited in the patient.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules such as a storage module, a communication module, etc. In some embodiments, two or more units in the processing device 140 may form one module. For example, the the synthetic image determination module 420, the scaling factor determination module 430, and/or the radiation dose deposition estimating module 440 may form a processing module. However, those variations and modifications also fall within the scope of the present disclosure.

Figure 5:
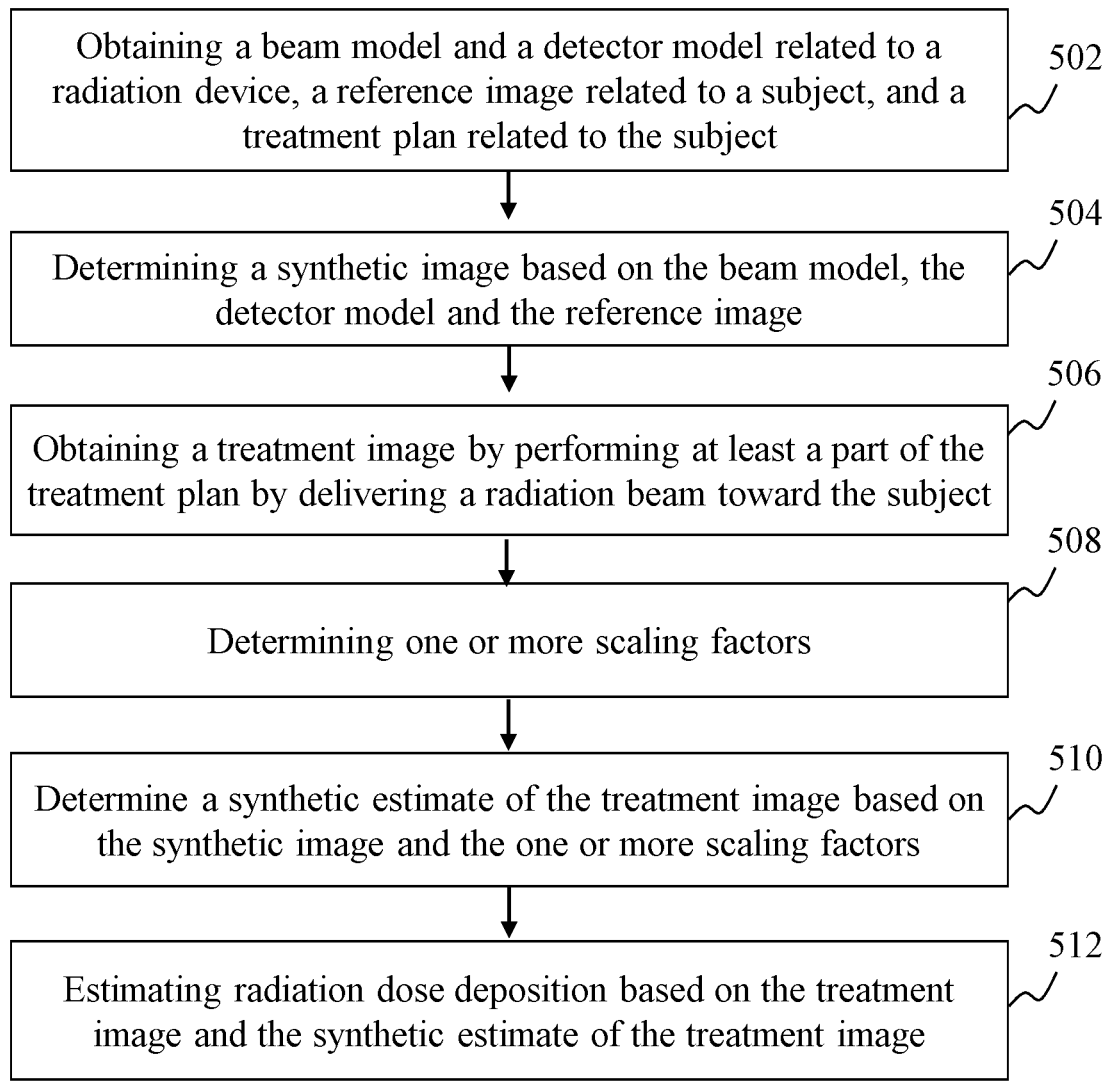
FIG. 5 is a flowchart illustrating an exemplary process for estimating radiation dose deposition according to some embodiments of the present disclosure.

FIG. 5 includes a flowchart illustrating an exemplary process for estimating radiation dose deposition according to some embodiments of the present disclosure. In some embodiments, at least a portion of process 500 may be performed by the processing device 140 (for example, implemented in the computing device 200 shown in FIG. 2).

In 502, a beam model and a detector model related to a radiation device, a reference image related to a subject, and a treatment plan related to the subject may be obtained. In some embodiments, 502 may be performed by the acquisition module 410. The radiation device may be or include the image-guided treatment apparatus 110 or a part of the image-guided treatment apparatus 110 (e.g., the treatment component of the image-guided treatment apparatus 110). In some embodiments, the beam model and the detector model related to the radiation device, the reference image related to the subject, and/or the treatment plan related to the subject may be obtained from a storage device capable of storing data (e.g., the storage device 150, cloud storage, etc.).

The beam model may be a mathematical characterization in terms of a plurality of parameters that describe the radiation therapy device (e.g., the image-guided treatment apparatus 110). The plurality of parameters may include or relate to, for example, the characteristics of the accelerator (e.g., energy spectrum, lateral beam quality variations) of the treatment component of the image-guided treatment apparatus 110, the shape(s) and position(s) of one or more radiation sources, and the geometry and material of a beam shaping device (e.g., a collimator system of the treatment component of the image-guided treatment apparatus 110).

In some embodiments, the beam model may be expressed in terms of a particle (e.g., photon, electron, positron, neutron, and/or ion) in a phase space, $\Phi(x,\theta,E,q,\eta)$, where x may represent a position of the particle, E may represent the energy of the particle, q may represent the charge of the particle (e.g., for electrons, q=−1, for positrons, q=1, for photons, q=0) or the type of the particle (e.g., q may be a non-physical index/label representing the particle type, such as q=0 for electron, q=1 for photon, q=2 for neutron, q=3 for proton), and $\theta$ may represent a travel direction of the particle, and $\eta$ may represent a weight of the particle that is used for radation transport modeling. For simplicity, a coordinate system may be established. The origin of the coordinate system may be represented as (u, v, w). The beam focal spot may be set at the origin of the coordinate system. The phase space may be a plane u, having in-plane coordinates (u, v) and a normal coordinate w along a central axis the beam (also referred to as beam central axis).

An entrance phase space plane, an exit phase space plane, and a detector phase space plane may be expressed according to Equations (1) through (3), respectively:

$$\Phi(x,\theta,E,q,\eta)_{ent}=\Phi(u,v,w=w_{ent},\theta,E,q,\eta), \quad (1)$$

$$\Phi(x,\theta,E,q,\eta)_{exit}=\Phi(u,v,w=w_{exit},\theta,E,q,\eta), \quad (2)$$

and $$\Phi(x,\theta,E,q,\eta)_{det}=\Phi(u,v,w=w_{det},\theta,E,q,\eta), \quad (3)$$

where $w_{ent}$, $w_{exit}$ and $w_{det}$ represent normal coordinates of the entrance phase space plane, the exit phase space plane, and the detector phase space plane, respectively. The entrance phase space plane may be a plane situated at a location at or before the beam enters the subject, which is perpendicular to the beam central axis. The exit phase space plane may be a plane at or after the beam exits the subject, which is perpendicular to the beam central axis. The detector phase space plane may be a plane where the detector is located, which is perpendicular to the beam central axis. It should be understood that representations other than a normal plane may also be used as manifolds upon which entry and exit radiation distributions may be employed. These manifolds may not need to be smooth or continuous in space.

A phase space may be described using a set of discrete particles. A discrete particle of a certain type at a position $u_0$, traveling along a direction $\theta_0$, with energy $E_0$, and a weight $\eta_0$ may be represented as Equation (4) in terms of a Dirac delta distribution:

$$\Phi(u_0,\theta_0,E_0,\eta_0)=\eta_0\delta(u-u_0,\theta-\theta_0,E-E_0). \quad (4)$$

For illustration purposes, in the disclosure below, expressions involving integrals over phase spaces may imply integration over sets of such delta distributions.

The detector model related to the radiation device may be used to generate a synthetic image based on the interation of particles with the detector. In some embodiments, the detector model may relate to at least one of a response of a detector to particles of a type, a response of the detector to particles of an energy level, an optical response of the detector, or a temporal response of the detector. The detector model may include one or more components. The one or more components may include an energy response function. The energy response function may represent the amount of energy that an incident particle of a type (e.g., photon, electron, positron, neutron, and/or ion) deposits in the detector (e.g., in one or more elements of the detector) as a function of the particle energy. In some embodiments, the detector model may also include other components that model other characteristics of the detector including, e.g., detector inter-frame lag and/or optical blurring.

Merely for purposes of illustration, the detector model may describe the energy deposition of an incident particle on the detector as a function of the charge of the particle and the angle of incidence of the particle with respect to the detector. In some embodiments, the detector model may be represented by $d(u,E,\theta,q)$. The incident particle may be a particle of a certain energy (before impinging on the detector), charge, and angle of incidence with respect to the detector (e.g., the detector plane). In some embodiments, radiation transport may be simulated directly based on a technique such as Monte Carlo (MC) simulation, without involving a detector model. In an external beam photon therapy, a detector model may be used to approximate a detector response to incident particles, neglecting the effects of different angles of incidence of the particles with respect to the detector (e.g., the detector plane) and the positions where the particles impinge on the detector plane. In some embodiments, the detector model may consider only d(E), the detected areal energy per particle of energy E (MeV), in the unit of, for example, $J/cm^2/(photon\ MeV)$, for patient treatment quality assurance (PQA) purposes, while neglecting the effects of detector inter-frame lag and/or opticle blurring.

The reference image related to the subject may be a planning image. The planning image may refer to an image of the subject according to which a treatment plan is made. The treatment plan may include a set of parameters describing how radiation is to be delivered to the subject, including, e.g., the beam dimension or the aperture size of a beam shaping device (e.g., a collimator system of the treatment component of the image-guided treatment apparatus 110), the radiation dose distribution (i.e., spatial distribution of the radiation dose), the radiation duration, the position of the radiation target in the subject of the treatment plan or a fraction thereof, or the like, or a combination thereof. The planning image may be used to identify a radiation target, tissue or one or more organs at risk, and the external contour (e.g., skin) of the subject or a portion thereof. Tissue attenuation values estimated based on the planning image may be converted to electron densities and used to estimate the radiation dose applied on the target.

The planning image may be an EPID image, a CT image, a fluoroscopy image, an ultrasound image, a PET image, a SPECT image, or an MR image. In some embodiments, the planning image may be a CT image generated by scanning the subject using a CT scanner. In some embodiments, the CT scanner may be a CBCT scanner and/or an MSCT scanner. The CBCT scanner may perform a CBCT scan of a subject. The MSCT scanner may perform an MSCT scan of a subject. The images generated based on the CBCT scan or the MSCT scan may be stored in a storage device in the radiation therapy system 100 for radiation therapy planning. In some embodiments, the planning image of the subject may be taken by the imaging component of the image-guided treatment apparatus 110. In some embodiments, the planning image of the subject may be taken using an imaging device other than the imaging component of the image-guided treatment apparatus 110. After the planning image of the subject is taken, a treatment plan may be designed for the subject based on the planning image.

The treatment plan may include one or more treatment fractions. For each of the treatment fraction, the radiation treatment plan may include a plurality of treatment parameters, such as a planned fraction duration, a planned radiation dose, a planned radiation energy delivery direction, a planned radiation energy beam shape, a planned radiation beam cross-sectional area, a planned region of interest (ROI) (e.g., the radiation target in the subject of the treatment plan), etc.

The treatment plan may describe radiation fields to be applied to the subject. The treatment plan may be set before a radiation therapy starts. The radiation therapy may be a photon-based radiation therapy, a brachytherapy, an electron beam therapy, a proton therapy, a neutron therapy, or the like, or any combination thereof. In some embodiments, the treatment plan may include a series of N fractions. In some embodiments, the beam shape of the n-th fraction may be $\Gamma_n$. Merely by way of example, a beam shape may be formed by a single conformation of the collimator system of the treatment component of the image-guided treatment apparatus 110, a composite of several conformations, an average of conformations over a time range, or an average of conformations over a gantry angle range. Each field may be associated with a radiation output quantity, such as a number (or count) of field monitor units (MUs) and a field MU-rate.

In 504, a synthetic image may be determined based on the beam model, the detector model, and the reference image. In some embodiments, the operation 504 may be performed by the synthetic image determination module 420.

The synthetic image may describe radiation energy deposited in the plane of the detector. In some embodiments, the reference image (e.g., CT image) may be converted to a representation of the distribution of radiation attenuation material(s) and the density or densities of the radiation attenuation material(s) as a function of a position x. For example, when MC simulation is used, a subject S(x) (e.g., a phantom (also referred to as "ph"), a treatment couch, a patient (also referred to as "pa")) may be represented by a material-type distribution $\mathcal{M}(x)$ and a density distribution $\rho(x)$. $\mathcal{M}(x)$ may be a function of the atomic composition of the subject at the position x. As another example, when an analytic primary projection model is used, the subject S(x) may be represented by a density-weighted attenuation distribution. For the subject S(x), the converted CT image may be represented as Equation (5):

$$\mu_w(x, E) = \mu_{ref}(x, E)\frac{\rho(x)}{\rho_{ref}(x)}, \quad (5)$$

where $\mu_w(x,E)$ represents an energy-dependent attenuation distribution for the subject, $\mu_{ref}(x,E)$ represents an energy-dependent attenuation distribution for a reference material, $\rho_{ref}$ represents a reference density of the reference material, and $\rho(x)$ represents an actual density distribution of the subject. The energy-dependent attenuation distribution of the reference material $\mu_{ref}(x,E)$ may represent the radiation attenuation due to the reference material when the reference material exhibits its reference density $\rho_{ref}$. If the subject is a patient or a part of the patient (e.g., an organ), the actual density distribution $\rho(x)$ of the subject may be estimated from a CT scan. If the subject is an object (e.g., a phantom), the actual density distribution $\rho(x)$ of the subject may be known.

The synthetic image may be determined based on the beam model, the detector model, and the reference image. In some embodiments, the synthetic image may be determined based on an exit radiation distribution in the plane of the detector $\Phi(x,\theta,E,q,\eta)_{det}$. Merely by way of example, the synthetic image may be determined according to Equation (6):

$$G^{p*}(u)=\int dE\Phi(u,E)_{det}P^*d(E), \quad (6)$$

where p* may be pa or ph, pa denotes a patient, and ph denotes a phantom. For simplicity, only one type of particles may be considered, and the detector response may be independent of the angle of incidence of the particles with respect to the detector plane (e.g., the angle of incidence of the particles with respect to the detector plane being neglected). In this case, the detector response may be dependent only upon energy of the incident particles. The weight $\eta$ may be suppressed from the notation. The values of pixels in the synthetic image may be expressed in J/history, which may be calculated using the simulation-calculated value of J/cm$^2$/history and the area of the pixel, where the number (or count) of histories may be that used to generate the entire phase space over the largest possible treatment field according to the treatment plan, a largest possible field that encompasses all fields in the plan, or a largest possible field that may be treated for any plan. A purpose of normalizing per the number (or count) of Monte Carlo simulation original particles (histories) run is that synthetic images may be scaled to actual doses. As used herein, the number (or count) of histories and original particles simulated are used interchangeably. For example, for radiotherapy beams, a unit of radiation output, such as a monitor unit (MU), may need to be calibrated to a certain dose measured within a standard phantom under a standard collimation and phantom placement condition. A Monte Carlo simulation of such a condition may yield a certain phantom dose per simulated original source particle history. In some embodiments, the number (or count) of particle histories does not correspond to the number (or count) of particles that deposit energy in the phantom at a standardized measurement region that determines the Gy/MU scale factor. As a consequence, synthetic images normalized to the number of original particle histories may have the advantage of potential independence of field size and shape, as long as the quality of the source beam remains constant, and field-size-dependent effects (e.g., backscatter into a monitor chamber of the image-guided treatment apparatus 110) and extrafocal radiation sources are negligible or have been compensated-for.

In some embodiments, the synthetic image may be generated by any technique that models radiation transport through the detector (e.g., MC simulation, Boltzmann transport equations). The synthetic image may be expressed using a discrete representation by dividing the image space into K discrete image elements. In some embodiments, each spatial element may correspond to a region $\Omega_k$. Each region may include an image pixel, or a group of image pixels.

The $k^{th}$ discrete image element of the synthetic image may be expressed according to Equation (7):

$$G^{p*}[\Omega_k] = \int du\, G^{p*}(u), u \in \Omega_k, \quad (7)$$

where $G_p^*[\Omega_k]$ denotes the $k^{th}$ discrete image element of the synthetic image in the unit of J/history/(area of $\Omega_k$). In cases where the image is composed of elements with equal areas (pixels of same sizes), the area normalization may be suppressed and the units J/history may be used. In cases where all synthetic images are generated for a source simulated using a single number of original source histories, the normalization may be suppressed by source history, and the unit J may be used, representing the energy deposited per pixel of the image, per original source history.

In 506, a treatment image may be obtained by performing at least a portion of the treatment plan on the subject. In some embodiments, the operation 506 may be performed by the acquisition module 410. The treatment image may also be referred to as a measured image. In some embodiments, the measured image may be an EPID image. The EPID image may be generated based on energy deposited in the EPID. In some embodiments, the deposited energy may be measured for each pixel of the EPID. The measured image may be represented by $M^{p*}(u)$, wherein p* may be pa (standing for a patient) or ph (standing for a phantom).

In some embodiments, the subject may include a living subject (e.g., a patient, an animal, an organ of a patient, etc) and a non-living subject (e.g., a phantom). The non-living subject may also be referred to as an object. In some embodiments, the subject may be a patient represented as $S^{pa}(x)$. When the at least a portion of the treatment plan is performed by delivering radiation to the patient $S^{pa}(x)$, a measured image $M^{pa}(u)$ may be obtained by performing the at least a portion of the treatment plan to the subject. Similarly, when the at least a portion of the treatment plan is performed by delivering radiation to a phantom, a measured image $M^{ph}(u)$ may be obtained. In some embodiments, the phantom $O^{ph}(x)$ may include air (no phantom), a treatment couch without a phantom present, a solid phantom such as a solid cylinder made of, e.g., uniform plastic, or the like, or any combination thereof.

In 508, one or more scaling factors may be determined. In some embodiments, the operation 508 may be performed by the scaling factor determining module 430.

The one or more scaling factors may represent a relationship between a measured image $M^{p*}(u)$ and a synthetic image $G^{p*}(u)$. In some embodiments, the one or more scaling factors may be determined under the condition that the measured image $M^{p*}(u)$ and the synthetic image $G^{p*}(u)$ are generated under a same imaging condition (e.g., a calibration condition). The scaling factor between a measured image $M^{p*}(u)$ and a synthetic image $G^{p*}(u)$ may be equal to the ratio of the value of a pixel in the measured image based on a signal detected by the real detector (or an average value of multiple pixels in the measured image) and the value of a corresponding pixel in the synthetic image estimated based on a simulated detector (or an average value of multiple pixels in the synthetic image). Merely by way of example, the calibration condition may be a 1 MU, 25×25 cm² radiation field incident on the detector, with the detector at w=145 cm. A pixel of an EPID image may have an area of 400×400 μm², and the energy deposited is digitized as an integer of 0 to 65,535. Under such a calibration condition, an MC simulation of H=$10^8$ particle histories may lead to an energy deposition of an average value of $10^{-15}$ J/pixel within a central 1 cm² of a simulated detector (a portion of the simulated detector located in a center region of the simulated detector whose area is 1 cm²). The synthetic detector may produce a value of $10^{-23}$ J/pixel/history within this region. A mean value of 57,600 may be measured per pixel on the actual detector within the same region. This may yield a scaling factor $\kappa$=57,600 MU$^{-1}$/($10^{-23}$ J/history).

In the case of a perfect model, the scaling factor may be determined according to Equation (8):

$$\kappa = \frac{M^{cali}(u)}{G^{cali}(u)}, \quad (8)$$

where $M^{cali}(u)$ represents the measured image under the calibration condition, and $G^{cali}(u)$ represents the synthetic image under the calibration condition.

The scaling factor $\kappa$ may be a constant in the case of the perfect model. The scaling factor $\kappa$ may be field-shape-independent (i.e., uncorrelated to the shape of the radiation field), and constant across the detector.

In some embodiments, the synthetic image may lack sufficient details to account for an output factor relating to, e.g., the size of the radiation field (also referred to as field size) and/or the shape of the radiation field (also referred to as field shape), or the like, or a combination thereof. Extra radiation that is backscattered by the collimator system such that the extra radiation enters the treatment component of the radiation therapy system 100 but fails to reach the subject or a portion thereof (e.g., the target of the subject), resulting in a variation of the value of $\kappa$ between different fields. In this case, the scaling factor may be dependent on the field shape. The scaling factor corresponding to a field with a shape $\Gamma_n$ may be calculated according to Equation (10):

$$\kappa_{\Gamma_n} = f\left[\frac{M^{pa}(u)}{M^{cali}(u)}\right], \quad (10)$$

where f may be a function, e.g., a mean function, that describes a mean value of scaling factors across a field. Thus, the scaling factor may be expressed according to Equation (11):

$$\kappa_{\Gamma_n} = \int du \frac{M^{pa}(u)}{M^{cali}(u)}, u \in \Gamma_n. \quad (11)$$

In some embodiments, the synthetic image may provide sufficient details such that ™ is field-shape-independent and $\kappa_{\Gamma_n}$ (n=1, 2, . . . ) may be determined. If the value of $\kappa_{\Gamma_n}$ is different from unity, it may be deemed that a radiation delivery error exists during the pretreatment evaluation compared to the treatment plan. As used herein, "close to" may indicate that the deviation of the value of $\kappa_{\Gamma_n}$ (n=1, 2, . . . ) from unity is less than a threshold, e.g., 30%, or 20%, or 10% of unity. In some embodiments, instead of checking whether $\kappa_{\Gamma_n}$ (n=1, 2, . . . ) is close to unity, it may be sufficient to check whether $\kappa_{\Gamma^i} = \kappa_{\Gamma^j}$ $\forall i,j$, i≠j in order to determine whether a radiation delivery error exists during the pretreatment evaluation compared to the treatment plan.

In 510, a synthetic estimate of the treatment image may be determined based on the synthetic image and the one or more scaling factors. In some embodiments, the synthetic estimate of the measured image may be determined based on the one or more scaling factors and the synthetic image. If the scaling factor is field-independent, the synthetic estimate of the treatment image may be expressed as $\hat{M}(u)=\kappa G(u)$. If the scaling factor is field-dependent, the synthetic estimate of the measured image may be $\hat{M}(u)=\kappa \cdot \kappa_{\Gamma_n} G(u)$.

In 512, radiation dose deposition may be estimated based on the treatment image and the synthetic estimate of the treatment image. In some embodiments, the operation 512 may be performed by the radiation dose deposition estimating module 440.

In some embodiments, radiation deposited in the patient may include primary radiation and scattered radiation. The primary radiation may also be referred to a primary component of the radiation. The scattered radiation may also be referred to as a scatter component of the radiation. In some embodiments, the primary component in the treatment image of a subject (e.g., the patient) may be determined by subtracting the scatter component from the measured image of the subject. In some embodiments, the scatter component may be estimated by an MC simulation based on the treatment plan, the beam model, the detector model, and the reference image of the subject. In the MC simulation, images due to primary radiation and scattered radiation may be synthesized separately. In some embodiments, the scatter component may be estimated iteratively using techniques such as scatter kernel superposition (SKS), which do not need to involve the estimation of the scatter component based on a CT image.

Once the scatter component is determined, the primary component may be estimated. In some embodiments, primary component of the synthetic estimate of the treatment image (also referred to as estimated treatment primary component or estimated measured primary component) may be determined according to Equation (12):

$$\hat{M}_{primary}^{p*}(u)=M^{p*}(u)-\hat{S}^{p*}(u), \tag{12}$$

where the $M^{p*}(u)$ may represent the treatment image, and $\hat{S}^{p*}(u)$ may represent the scatter component, $\hat{M}_{primary}^{p*}(u)$ may denote the estimated treatment primary component, and p* may be pa (standing for a patient) or ph (standing for a phantom).

In some embodiments, if the scatter component is estimated by means of a scatter-to-primary ratio (SPR), the estimated treatment primary may be determined according to Equation (13):

$$\hat{M}_{primary}^{P*}(u) = \frac{M^{P*}(u)}{1+\widehat{SPR}^{P*}(u)}, \tag{13}$$

where the $M^{P*}(u)$ may represent the treatment image, and $\widehat{SPR}^{P*}(u)$ may represent the SPR. In some embodiments, the SPR may be calculated using techniques such as MC simulation, iterative SKS, one-pass SKS, etc. The SPR may be a dimensionless value.

In some embodiments, the radiation dose deposited in the patient may be estimated based on the estimated treatment primary component of the subject. Detailed descriptions regarding the determination of the radiation dose deposition may be disclosed elsewhere in the present disclosure. See, for example, FIG. 6 and the descriptions thereof.

It should be noted that the above descriptions of process 500 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

For example, the radiation dose deposited within the patient may be estimated by adjusting at least one of the field shape, the field MU, and the field MU rate based on the recorded field shape. In some embodiments, the field MU may be adjusted between a measured field MU and an expected field MU. In some embodiments, the field MU rate may also be adjusted between a measured field MU rate and an expected field MU rate. The adjusted field shape, field MU and/or field MU rate may be input into a forward radiation transport model to calculate the dose deposited in the patient.

The forward radiation transport model may be embodied by an algorithm that is used in a treatment planning system to calculate radiation dose deposition. Exemplary algorithms may include a pencil beam algorithm, a convolution-superposition kernel-based algorithm, MC simulation, an algorithm based on Boltzmann transport equations. The algorithm may take an energy fluence map of a radiation beam that is incident on the subject as an input. A primary image may be obtained by removing the scatter component from the EPID image. The primary image may be "reverse attenuated" through the subject CT volume by mapping the subject CT volume to an analytic x-ray transmission map for the incident primary beam (the incident radiation beam minus the scatter component). The energy fluence map of the radiation beam and/or the analytic x-ray transmission map may be estimated based on Beer's law and linear attenuation coefficients of the materials within the subject. The linear attenuation coefficients may be energy dependent. The linear attenuation coefficients may be determined by multiplying the mass attenuation coefficients for the materials in the CT (in, for example, units of $cm^2/g$) by a local density (in, for example, units of $g/cm^3$), to produce the linear attenuation coefficients in, for example, units of $cm^{-1}$. The local density may be estimated from the Hounsfield unit (HU) or CT numbers of the CT based on a calibration curve that maps HU to electron density. Materials (e.g., bone, soft tissue, lung) may be classified based on HU values. The use of dual energy/spectral CT soley, or in combination of MR images, may enable a superior performance on material identification and density estimation. Segmentation and/or atlas based methods may also be employed to improve the performance on material identification, thus improving the accuracy of the linear attenuation coefficients. In some embodiments, a planned energy fluence map may be multiplied by a detector energy response function, and integrated over energy distribution of the incident beam in order to produce an entrance fluence image that may be directly compared to an estimated entrance fluence obtained based on the EPID image and a CT image of the subject. In some embodiments, the planned energy fluence map may be multiplied by a transmission map, which may describe the propagation of the incident primary beam through the subject), then multiplied by the detector energy response function, and integrated over energy levels of the incident primary beam to obtain an image. The obtained image may be directly compared with the primary image estimated from the EPID image. The comparison of the obtained image and the primary image may indicate differences in the field shape, since the optical blurring effect of radiation scattering in the subject are reduced. Overdosing or underdosing of a region of the subject may also be more readily detected and compensated for similar reasons.

Figure 6:
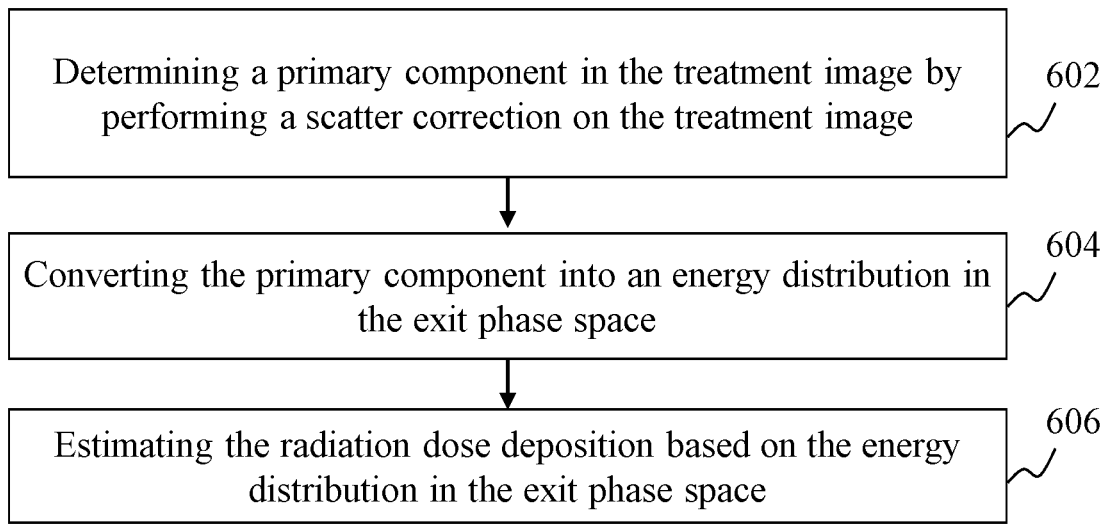
FIG. 6 is a flowchart illustrating an exemplary process for estimating radiation dose deposition according to some embodiments of the present disclosure.

FIG. 6 is a flowchart illustrating an exemplary process for estimating radiation dose deposition according to some embodiments of the present disclosure. In some embodiments, at least a portion of process 600 may be performed by the processing device 140 (for example, implemented in the computing device 200 shown in FIG. 2). In some embodiments, the operations 602 through 606 may be performed by the radiation dose deposition estimating module 440.

In 602, primary component in the treatment image may be determined by performing a scatter correction on the treatment image. In some embodiments, the operation 602 may be performed by the radiation dose deposition estimating module 440. The treatment image may include a primary component and a scatter component. In some embodiments, the scatter correction may be performed on the treatment image. Exemplary scatter correction techniques may include a convolution technique, a deconvolution technique, an ordered subsets convex technique, an MC technique, a beam-stop measurement technique, or the like, or any combination thereof.

In 604, the primary component may be converted into an energy distribution in the exit phase space. In the plane that the ray exits the body of the patient (i.e., the exit phase space plane), the estimated treatment primary may be converted into the energy distribution in the exit phase space according to the Equation (14):

$$\hat{M}_{primary}^{pa}(u,\eta)=\kappa \int dE \; d(E) \hat{\Phi}_{\Gamma^n}(u,E,\eta)_{exit}, \quad (14)$$

where $\hat{\Phi}(u,E,\eta)_{exit}$ may denote the exit phase space.

In 606, the radiation dose deposition may be determined based on the energy distribution in the exit phase space. The radiation dose deposition may be the energy distribution in the entrance phase space plane that may be delivered to the patient during radiation therapy. In order to determine the energy distribution in the entrance phase space plane, the entrance phase space $\hat{\Phi}(u,E,\eta)_{ent}$ may be determined. In some embodiments, the entrance phase space $\hat{\Phi}(u,E,\eta)_{ent}$ may be determined based on the exit phase space determined according to Equation (14). For example, the entrance phase space may be calculated according to the Equation (15):

$$\hat{\Phi}_{\Gamma^n}(u, E, \eta)_{ent} = \hat{\Phi}_{\Gamma^n}\left(\frac{w_{exit}}{w_{ent}}e, E, \eta'\right)_{exit}, \quad (15)$$

where $w_{exit}$ may represent a normal coordinate of the exit phase space plane along the beam central axis, $w_{ent}$ may represent a normal coordinate of the entrance phase space plane along the beam central axis, and η' may represent the weight corresponding to the exit phase space plane. The estimated entrance phase space that led to the measured exit image may be compared to that intended for delivery. η' may be determined according to Equation (16):

$$\eta'=\eta e^{\int dl \; \mu^P *(x,E)}. \quad (16)$$

It should be understood that the method of using the weight to represent attenuation and inverse attenuation, apart from being a convenient means of mathematical representation, may also provide an explicit and advantageous means of calculation and data storage representation. However, it should be understood to be simply some embodiments of a means of representing and performing an attenuation or inverse attenuation operation.

In some embodiments, the energy distribution in the entrance phase space plane may be determined by inverting the Equation (14). In some embodiments, a beamlet parameter space (BPS) method may be used to invert the Equation (14).

In the BPS method, the entire (full field) entrance phase space may be projected through the patient CT, and the entire exit phase space may be determined. The entire exit phase space may be determine according to Equation (16):

$$\Phi(u,E,\eta)_{exit}=\Phi_{full}(u,E,\eta)e^{\int dl \; \mu^P *(x,E)}_{ent}, \quad (16)$$

where μ denotes the linear attenuation coefficient of the material at point x in the patient/phantom volume for particles with energy E.

The image space may be divided into K discrete image elements, and each image element may be assigned a variable $\omega_\kappa$, where κ=0, 1, . . . , K. $\omega_\kappa$ represents a region intensity of a region (generalized pixel) related to the deposition of energy in that region. In some embodiments, discrete image elements may be assigned to regions of the radiation field with non-zero intensities. Within the k-th region $\omega_k$, the phase space may be expressed as Equation (17):

$$\Phi_{full}[\kappa]=\Phi_{full}(u \in \Omega_k, E)_{exit}. \quad (17)$$

The region of the estimated primary image (derived from the measured image) corresponding to $\Omega_k$ may be expressed as Equation (18):

$$\hat{M}_{primary}^{pa}[\kappa]=\int du \hat{M}_{primary}^{pa}, u \in \Omega_k. \quad (18)$$

Further, $\hat{w}_k$, which denotes an estimated region intensity, may be determined according to Equation (19):

$$\hat{w}_k = \frac{\hat{M}_{primary}^{pa}[\kappa]}{\kappa \int dE \; d(E) \Phi_{full}[\kappa]}. \quad (19)$$

The estimated treatment primary may be determined according to Equation (20) in combination of a discretized version of the Equation (14):

$$\hat{M}_{primary}^{pa}=\kappa \int dE \; d(E) \hat{\Phi}_{\Gamma^n}[\kappa]_{exit}=\kappa \widehat{W}_\kappa \int dE \; \overline{d(E)} \; \Phi_{full}[\kappa]. \quad (20)$$

According to the Equation (20), it may be concluded that, $$\hat{\Phi}_{\Gamma^n}[\kappa]_{exit}=\widehat{W}_\kappa \Phi_{full}[\kappa]. \quad (21)$$

The entrance phase space may be determined by incorporating Equation (21) into Equation (15). Further, the radiation dose deposition may be determined.

It should be noted that the above descriptions of process 600 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

For example, the primary component in the treatment image may be estimated according to Equation (13). As another example, the BPS method used in the operation 606 may be substituted by a collimator parameter space (CPS) method. According to the CPS method, the field MU and collimator positions may be optimized to produce a synthetic primary image being close to $\hat{M}_{primary}^{pa}$.

If the set of radiation output, gantry positions and collimator conformations is represented as C. For example, C may represent a sequence of gantry positions. Each gantry position may be associated with a sequence of MLC shapes, jaw positions, and collimator angles. One or more optimal delivery parameters used for predicting the estimated primary component may be determined according to Equation (22):

$$\hat{C}_\Gamma^n = \underset{C}{\operatorname{argmin}} \int du \Big[ \kappa \int dE\, d(E) \Phi_{\Gamma^n}(u, E; C)_{det} - \hat{M}_{primary}^{pa}(u) \Big]^2. \qquad (22)$$

Equation (22) may be interpreted as: "find that machine configuration that makes the estimated synthetic image closest to the estimate of the measured primary image (which is based on the measured image due to the primary component and the scatter component)." Merely by way of example, one measured image may correspond to a single gantry angle, a single jaw position, a single MLC shape, and a single collimator angle. Solutions of Equation (22) may be used to estimate the gantry angle, jaw position, MLC shape, and collimator angle by iteratively synthesizing images for different parameter vectors C with the objective of minimizing the discrepancy between the synthetic image and the primary component of the measured image. In some embodiments, a plurality of iterations may be performed for obtaining a smallest discrepancy between the primary component in the treatment image and the synthetic image. During each of the plurality of iterations, a gantry position may be scheduled. The gantry position may be associated with a sequence of MLC shapes, jaw positions, and collimator angles. After the plurality of iterations are performed, an optimal gantry position corresponding to a smallest discrepancy between the primary component in the treatment image and the synthetic image may be determined. Note that, while it is possible to have the objective of minimizing the discrepancy between the synthetic images and the total (primary and scatter) measured image, this may be less convenient, since scatter may need to be estimated at each iteration of the optimization).

In some embodiments, L2 norm (i.e., Euclidean norm, which is used as a standard quantity for measuring a vector difference) may be used to predict the estimated treatment primary component. As explained above, in some embodiments, the total (primary plus scatter) image may be synthesized in the forward model and compared to the total measured image within the norm.

Figure 7:
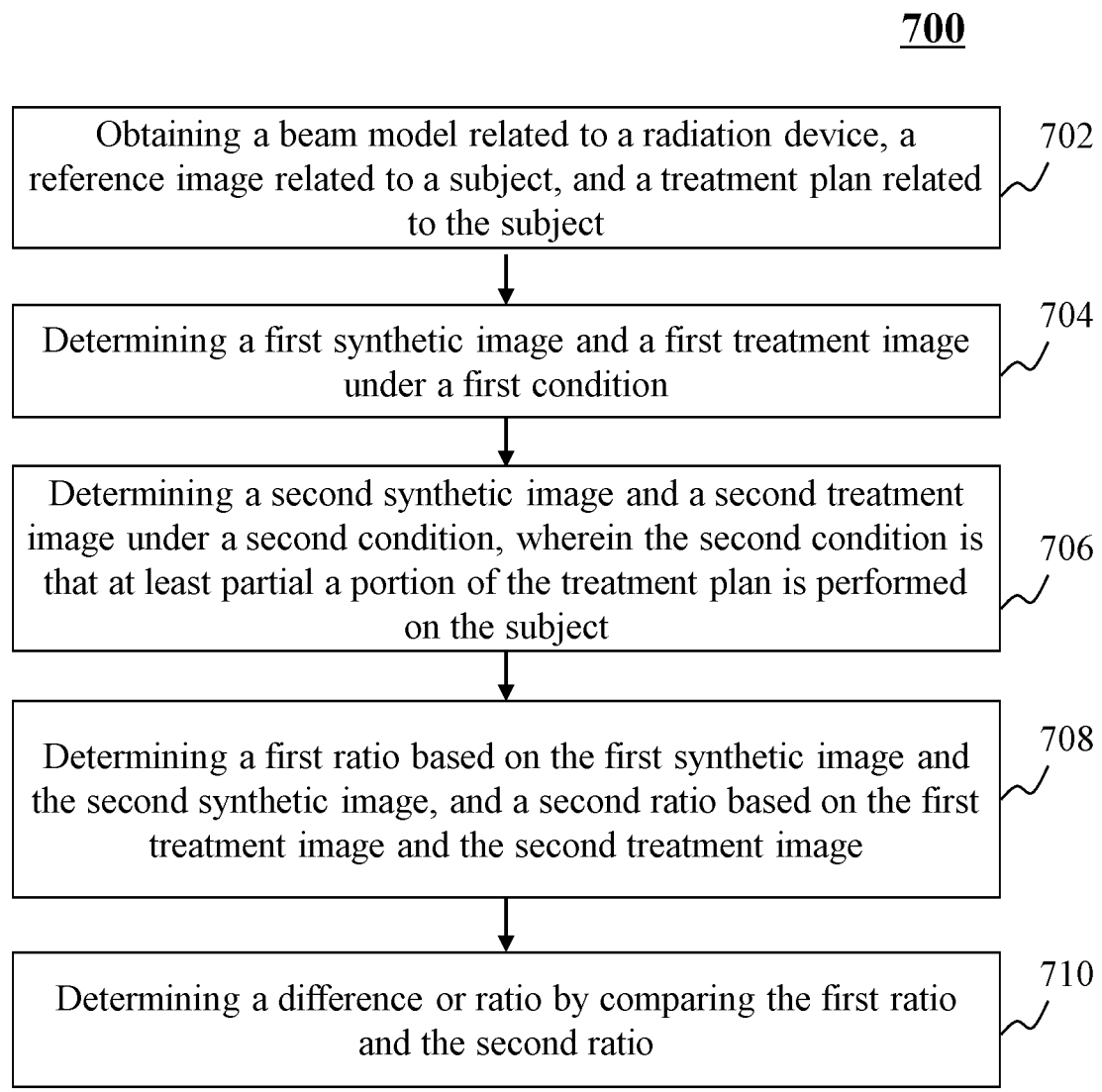
FIG. 7 is a flowchart illustrating an exemplary process for detecting errors in a radiation therapy according to some embodiments of the present disclosure.

FIG. 7 is a flowchart illustrating an exemplary process for detecting errors in a radiation therapy by comparing a first ratio and a second ratio according to some embodiments of the present disclosure. In some embodiments, at least a portion of the process 700 may be performed by the processing device 140 (for example, implemented in the computing device 200 shown in FIG. 2). In some embodiments, the process 700 may be performed before the delivery of a treatment fraction. In some embodiments, the process 700 may be performed periodically before each treatment fraction, or every other treatment fraction, etc.

In 702, a beam model related to a radiation device, a reference image related to a subject, and a treatment plan related to the subject may be obtained. In some embodiments, the operation 702 may be performed by the acquisition module 410. In some embodiments, the operation 702 may be the same as or similar to the operation 502.

In 704, a first synthetic image and a first treatment image under a first condition may be determined. In some embodiments, the operation 704 may be performed by the synthetic image determination module 420.

In some embodiments, the first condition may be a condition under which at least a portion of the treatment plan is performed without the subject. For example, the treatment plan may be performed on an phantom. The phantom may include air (no phantom), a treatment couch without any phantom present, a solid cylinder phantom made of, for example, uniform plastic, or the like, or any combination thereof.

The first synthetic image may describe the energy deposited in the plane of the detector under the first condition. The first synthetic image may be represented as $G^{ph}(u)$. The first treatment image may be a measured image generated when the radiation is delivered to the phantom. For example, the treatment image may be an EPID image of the phantom, which is represented as $M^{ph}(u)$. In some embodiments, the determination of the first synthetic image and the first measured image in 704 may be the same as or similar to the operations 504 and 506.

In 706, a second synthetic image and a second treatment image under a second condition may be determined, wherein the second condition is a condition under which at least a portion of the treatment plan is performed on the subject. In some embodiments, the operation 706 may be performed by the synthetic image determination module 420.

The second synthetic image may describe the energy deposited in the plane of the detector under the second condition. The second synthetic image may be represented as $G^{pa}(u)$. The second treatment image may be a measured image generated when the radiation is delivered to a living subject. For example, the second treatment image may be an EPID image of the patient, which may be represented as $M^{pa}(u)$. In some embodiments, the determination of the second synthetic image and the second measured image in 704 may be the same as or similar to the operations 504 and 506.

In some embodiments, the second condition may be a condition that at least a portion of the treatment plan is performed on the subject. In some embodiments, the first condition and the second condition may be at the same field MU rate and frame rate. In this case, the first condition and the second condition may correspond to similar detector lag characteristics.

In some embodiments, the treatment plan may be performed twice on the phantom. For the first time, an original field MU rate may be used. For the second time, the original field MU rate may be modified by accounting for different attenuation of the patient with respect to the phantom (or lack thereof). In this way, the detector may be subject to a similar intensity per unit time (proportional to deposited energy per unit time) for the two times. The advantage may be that this may model the lag effect better than non-patient-specific and non-plan-specific correction methods.

In 708, a first ratio may be determined based on the first synthetic image and the second synthetic image, and a second ratio may be determined based on the first treatment image and the second treatment image. In some embodiments, the operation 710 may be performed by the scaling factor determination module 430.

The first ratio may be determined according to Equation (22):

$$\hat{R}(u) = \frac{G^{pa}(u)}{G^{ph}(u)}, \qquad (22)$$

where $\hat{R}(u)$ denotes the first ratio. The second ratio may be determined according to Equation (23):

$$R(U) = \frac{M^{pa}(u)}{M^{ph}(u)}, \qquad (23)$$

where $R(u)$ denotes the second ratio.

In 710, a difference or ratio may be determined by comparing the first ratio and the second ratio. By comparing the first ratio and the second ratio using the difference or the ratio, a plurality of errors in the radiation therapy may be detected. The plurality of errors may include errors in the field shape, and errors in an intensity modulation pattern, errors in patient setup, such as anatomy not as planned, wrong patient, anatomy, setup error, errors in beam quality, such as wrong energy, wrong flat/unflat beam selection, wrong beam profile, wrong beam spectrum, and discrepancies between dose delivered to the phantom and the patient. In a first example, the MLC shape may be significantly different between planned and delivery cases, which may clearly cause the ratio image $R(u)$ to be different from $\hat{R}(u)$ in regions where the field shape is mismatched. This is because $\hat{R}(u)$ was synthesized using the planned field shape. In a second example, the patient may be wrongly positioned, so that a bone of the patient may present in the field at the time of the radiation treatment, but not in the treatment plan. Since $G^{pa}(u)$ does not reflect the presence of the bone, $\hat{R}(u)$ may be different from $R(u)$, since $\hat{R}(u)$ is generated from the planning CT where the bone was not present in the planned field. In a third example, a flattening-filter-free 6 MV beam is used to deliver radiation to the patient, but the planned beam was a 10 MV flattened beam, indicating the use of incorrect beam quality. Although the field shapes may remain unchanged, the change in beam attenuation through the patient may be reflected in $R(u)$ being different from the expected $\hat{R}(u)$, which is based on the planned beam quality. In a fourth example, incorrect MU may be delivered both during the formation of $M^{pa}$ and $M^{ph}$. The ratio method (i.e., the method described in the process 700) may be unable to detect such an error. However, the ratio method, in combination with standard routine QA procedures that verify the Gy/MU produced by a beam generated by the radiation therapy system (such as recommended by AAPM TG-142), may detect such an error. A combination of a ratio method with an absolute dose measurement of a single field at the time of measuring either $M^{pa}$ or $M^{ph}$ may also be sufficient to detect such errors.

The ratio method has the advantage that many modeling errors and deficiencies cancel-out. For example, if the detector frame-lag affects the pretreatment and treatment images equally, it is not necessary to model this effect in order to predict the ratio of images. Similarly, there is no need to model or compensate for any output factor or other field-size-dependent factors that can be difficult to know exactly. This greatly reduces the complexity of commissioning an EPID dosimetry system.

It should be noted that the above descriptions of process 700 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

For example, a third ratio and a fourth ratio may further be determined. The third ratio may be determined based on a primary component of the first synthetic image and a primary component of the second synthetic image. The fourth ratio may be determined based on a primary component of the first treatment image and a primary component of the second treatment image. The primary component of the first synthetic image, the second synthetic image, the first treatment image, and the second treatment image may be determined according to, for example, Equation (13). The third ratio may be determined according to Equation (24):

$$\hat{\tau}(u) = \frac{\hat{G}^{pa}_{primary}(u)}{\hat{G}^{ph}_{primary}(u)}, \qquad (24)$$

where $\hat{\tau}(u)$ may denote the third ratio.

The fourth ratio may be determined according to Equation (25):

$$\tau(u) = \frac{\hat{M}^{pa}_{primary}(u)}{\hat{M}^{ph}_{primary}(u)}, \qquad (24)$$

where $\tau(u)$ may denote the fourth ratio.

A difference or ratio may be determined by comparing the third ratio and the fourth ratio. By comparing the third ratio and the fourth ratio through the difference or the ratio, a plurality of errors in the radiation therapy may be detected. The plurality of errors may include errors in the field shape, and the intensity modulation pattern, errors in patient setup, such as anatomy not as planned, wrong patient, anatomy, setup error, errors in beam quality, such as wrong energy, wrong flat/unflat beam selection, wrong beam profile, wrong beam spectrum, and discrepancies between dose delivered to the patient and the phantom. Since the scatter component is eliminated, a greater sensitivity to the errors may be obtained.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
    at least one storage medium including a set of instructions; and
    at least one processor configured to communicate with the at least one storage medium, wherein when executing the set of instructions, the system is directed to perform operations including:
        obtaining a beam model and a detector model related to a radiation device, a reference image related to a subject, and a treatment plan related to the subject;
        determining a synthetic image based on the beam model, the detector model, and the reference image;

obtaining a treatment image by performing at least a portion of the treatment plan including delivering at least a radiation beam toward the subject using the radiation device;

determining one or more scaling factors representing a relationship between the synthetic image and the treatment image;

determining a synthetic estimate of the treatment image based on the synthetic image and the one or more scaling factors; and estimating radiation dose deposition based on the treatment image and the synthetic estimate of the treatment image.

2. The system of claim 1, wherein to estimate radiation dose deposition based on the treatment image and the synthetic estimate of the treatment image, the system is further directed to perform the operations including:

determining a difference or ratio between the treatment image and the synthetic estimate of the treatment image.

3. The system of claim 1, wherein the system is further directed to perform the operations including:

determining a primary component in the treatment image by performing a scatter correction of the treatment image, wherein the estimating radiation dose deposition is performed based on the primary component in the treatment image.

4. The system of claim 3, wherein to estimate the radiation dose deposition based on the primary component in the treatment image and the synthetic estimate of the treatment image, the system is further configured to perform the operations including:

converting the primary component into an energy distribution in an exit phase space; and estimating the radiation dose deposition based on the energy distribution in the exit phase space.

5. The system of claim 4, wherein to estimate the radiation dose deposition based on the energy distribution in the exit phase space, the system is further configured to perform the operations including:

in a plurality of iterations,
determining an optimal gantry position corresponding to a smallest discrepancy among discrepancies between the primary component in the treatment image and the synthetic image in the plurality of iterations, wherein the optimal gantry position is associated with a sequence of MLC shapes, jaw positions, and collimator angles.

6. The system of claim 1, wherein the beam model relates to at least one of an energy of particles of the radiation beam, charges of the particles, types of the particles, or travel directions of the particles.

7. The system of claim 1, wherein the detector model relates to at least one of a response of a detector of the radiation device to particles of a type, a response of the detector to particles of an energy level, an optical response of the detector, or a temporal response of the detector.

8. The system of claim 1, wherein the detector model relates to a material of a detector of the radiation device and a density distribution of the material of the detector.

9. The system of claim 1, wherein the one or more scaling factors relate to different shapes of one or more fields or segments of the treatment plan.

10. A method implemented on a computing apparatus having at least one processor and at least one computer-readable storage device, the method comprising:

obtaining a beam model and a detector model related to a radiation device, a reference image related to a subject, and a treatment plan related to the subject;

determining a synthetic image based on the beam model, the detector model, and the reference image;

obtaining a treatment image by performing at least a portion of the treatment plan including delivering at least a radiation beam toward the subject using the radiation device;

determining one or more scaling factors representing a relationship between the synthetic image and the treatment image;

determining a synthetic estimate of the treatment image based on the synthetic image and the one or more scaling factors; and estimating radiation dose deposition based on the treatment image and the synthetic estimate of the treatment image.

11. The method of claim 10, the estimating radiation dose deposition based on the treatment image and the synthetic estimate of the treatment image including:

determining a difference or ratio between the treatment image and the synthetic estimate of the treatment image.

12. The method of claim 10, further including:

determining a primary component in the treatment image by performing a scatter correction of the treatment image, wherein the estimating radiation dose deposition is performed based on the primary component in the treatment image.

13. The method of claim 12, the estimating the radiation dose deposition based on the primary component in the treatment image and the synthetic estimate of the treatment image including:

converting the primary component into an energy distribution in an exit phase space; and estimating the radiation dose deposition based on the energy distribution in the exit phase space.

14. The method of claim 13, the estimating the radiation dose deposition based on the energy distribution in the exit phase space including:

in a plurality of iterations,
determining an optimal gantry position corresponding to a smallest discrepancy among discrepancies between the primary component in the treatment image and the synthetic image in the plurality of iterations, wherein the optimal gantry position is associated with a sequence of MLC shapes, jaw positions, and collimator angles.

15. The method of claim 10, wherein the beam model relates to at least one of an energy of particles of the radiation beam, charges of the particles, types of the particles, or travel directions of the particles.

16. The method of claim 10, wherein the detector model relates to at least one of a response of a detector of the radiation device to particles of a type, a response of the detector to particles of an energy level, an optical response of the detector, or a temporal response of the detector.

17. A system, comprising:
at least one storage medium including a set of instructions; and
at least one processor configured to communicate with the at least one storage medium, wherein when executing the set of instructions, the system is directed to perform operations including:

obtaining a beam model related to a radiation device, a reference image related to a subject, and a treatment plan related to the subject;

determining a first synthetic image and a first treatment image under a first condition;

determining a second synthetic image and a second treatment image under a second condition, wherein the second condition is that at least a portion of the treatment plan is performed on the subject;

determining a first ratio based on the first synthetic image and the second synthetic image;

determining a second ratio based on the first treatment image and the second treatment image;

determining a difference or ratio by comparing the first ratio and the second ratio; and detecting an error in a radiation therapy based on the difference or the ratio.

18. The system of claim 17, wherein the first condition is that at least part of the treatment plan is performed on an object.

19. The system of claim 17, wherein the first synthetic image is determined by simulating a first imaging condition of the first treatment image, and the second synthetic image is determined by simulating a second imaging condition of the second treatment image.

20. The system of claim 17, wherein the error includes at least one of an error in a field shape and an intensity modulation pattern, an error in patient setup, or an error in beam quality.

\* \* \* \* \*